US00PP22079P3

(12) United States Plant Patent
Pait et al.

(10) Patent No.: US PP22,079 P3
(45) Date of Patent: Aug. 16, 2011

(54) SLASH PINE TREE NAMED 'CF PS1-3352'

(50) Latin Name: *Pinus elliottii*
Varietal Denomination: CF PSI-3352

(75) Inventors: John Pait, Atlanta, GA (US); Stephen Attree, Victoria (CA); Plamen Denchev, Victoria (CA); Robert Weir, Cary, NC (US); Andy Benowicz, Victoria (CA)

(73) Assignee: Cellfor Inc., Saanichton, British Columbia (CA)

( * ) Notice: Subject to any disclaimer, the term of this patent is extended or adjusted under 35 U.S.C. 154(b) by 0 days.

(21) Appl. No.: 12/456,829

(22) Filed: Jun. 23, 2009

(65) Prior Publication Data

US 2010/0325764 P1 Dec. 23, 2010

(51) Int. Cl.
*A01H 5/00* (2006.01)

(52) U.S. Cl. ..... Plt./213

(58) Field of Classification Search ..... Plt./213
See application file for complete search history.

*Primary Examiner* — Annette Para

(74) *Attorney, Agent, or Firm* — Michael Best & Friedrich LLP

(57) ABSTRACT

A new and distinctive variety of a slash pine tree which has been denominated varietally as 'CF PS1-3352' which is distinguished by high growth rate, good resistance to fusiform rust and pitch canker, excellent stem straightness, medium crown width, long stem internodes, flat to medium branch angle and medium branch diameter.

2 Drawing Sheets

Latin name: *Pinus elliottii.*
Variety denomination: 'CF PS1-3352'.

BACKGROUND

A new variety of slash pine tree (*Pinus elliottii* Engelm.) has been discovered. This selection has been designated as 'CF PS1-3352.'

This new variety is a progeny of two first generation selections. Female parent is a first generation selection made in Taylor County, Fla. Male parent is a first generation selection made in Wayne County, Ga.

Cross pollination occurred in early 1998 followed by induction and cryopreservation of embryogenic tissue in 1999. First somatic seedlings were produced in 2000 and planted in early 2001 in three field experiments. A total of 15 ramets were planted at 5 ramets per field experiment. The field experiments are located in Florida and Georgia.

BRIEF SUMMARY

A new and distinct cultivar of slash pine (*Pinus elliottii*) is distinctly characterized by high growth rate, good resistance to fusiform rust and pitch canker, excellent stem straightness, medium crown width, long stem internodes, flat to medium branch angle, medium branch diameter and which is mature for commercial harvesting sooner than conventionally grown trees under the ecological conditions prevailing the Atlantic and Gulf Coastal Plains of the United States.

The *Pinus elliottii* plants of this variety were asexually propagated using an advanced form of micropropagation called somatic embryogenesis carried out at a production facility in Victoria, Canada. Somatic embryogenesis uses a complex process which relies on the splitting of one embryo into many identical embryos. Somatic embryos can then be grown into plants which are all identical genetically. The asexual propagation occurs at an earlier stage in the plant's life cycle than most other micropropagated plants. The detailed methods for somatic embryogenesis used for asexually propagating conifers in general are described in U.S. Pat. No. 6,372,496 and for slash pine in particular in U.S. Patent Application Publication No. 2004/0203150.

BRIEF DESCRIPTION OF THE DRAWINGS

The drawings are color photographs showing the new variety of slash pine.

DETAILED BOTANICAL DESCRIPTION

Figure 1:
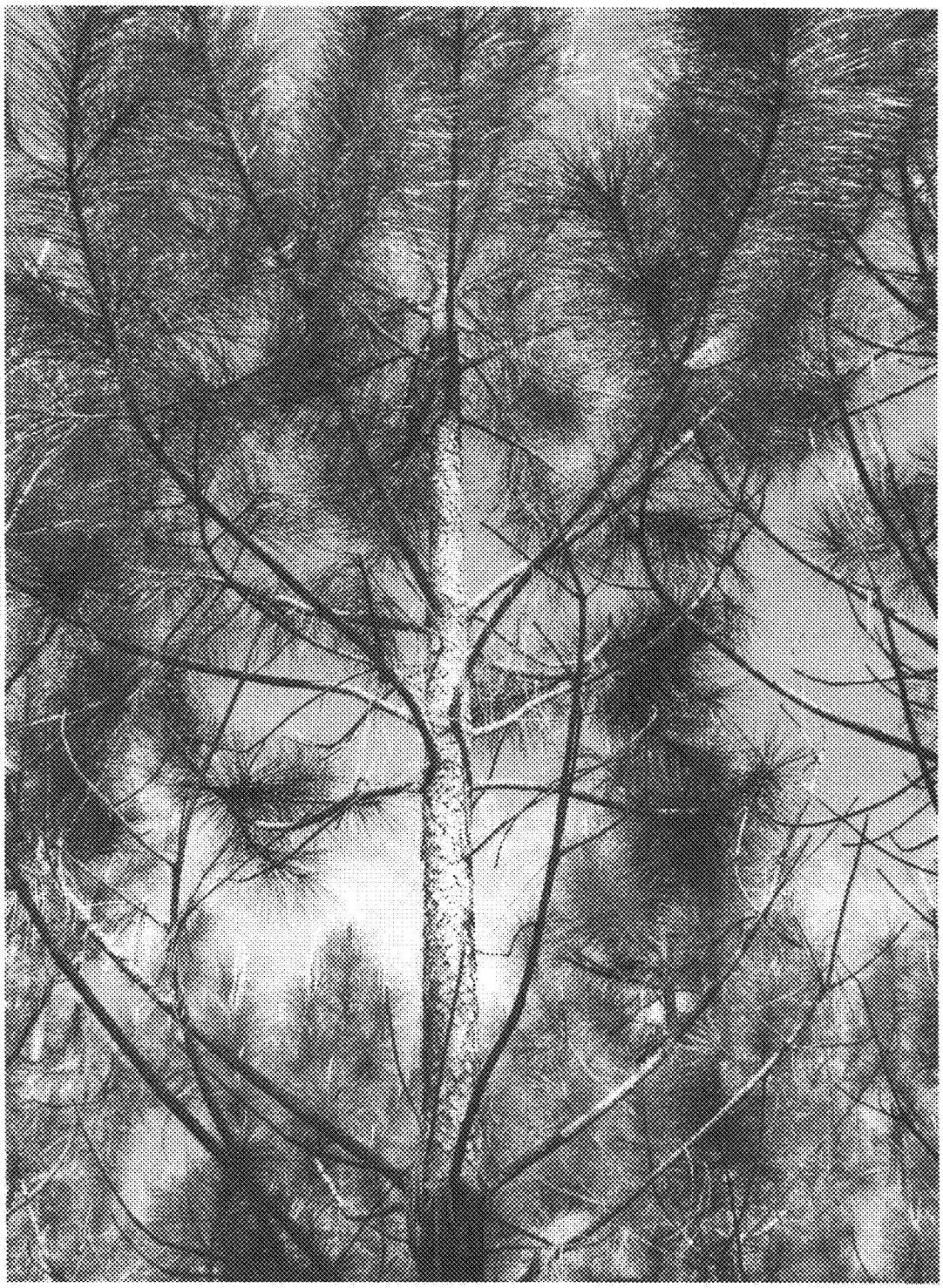
FIG. 1 is a photograph showing 'CF PS1-3352' ramet # 2 planted in Nassau, Fla. The picture was taken after seven field growing seasons. The picture shows excellent stem straightness, distinctive long internodes, medium to flat branch angle between the stem and the branches, and medium branch diameter (relative to the size of the stem).
Figure 2:
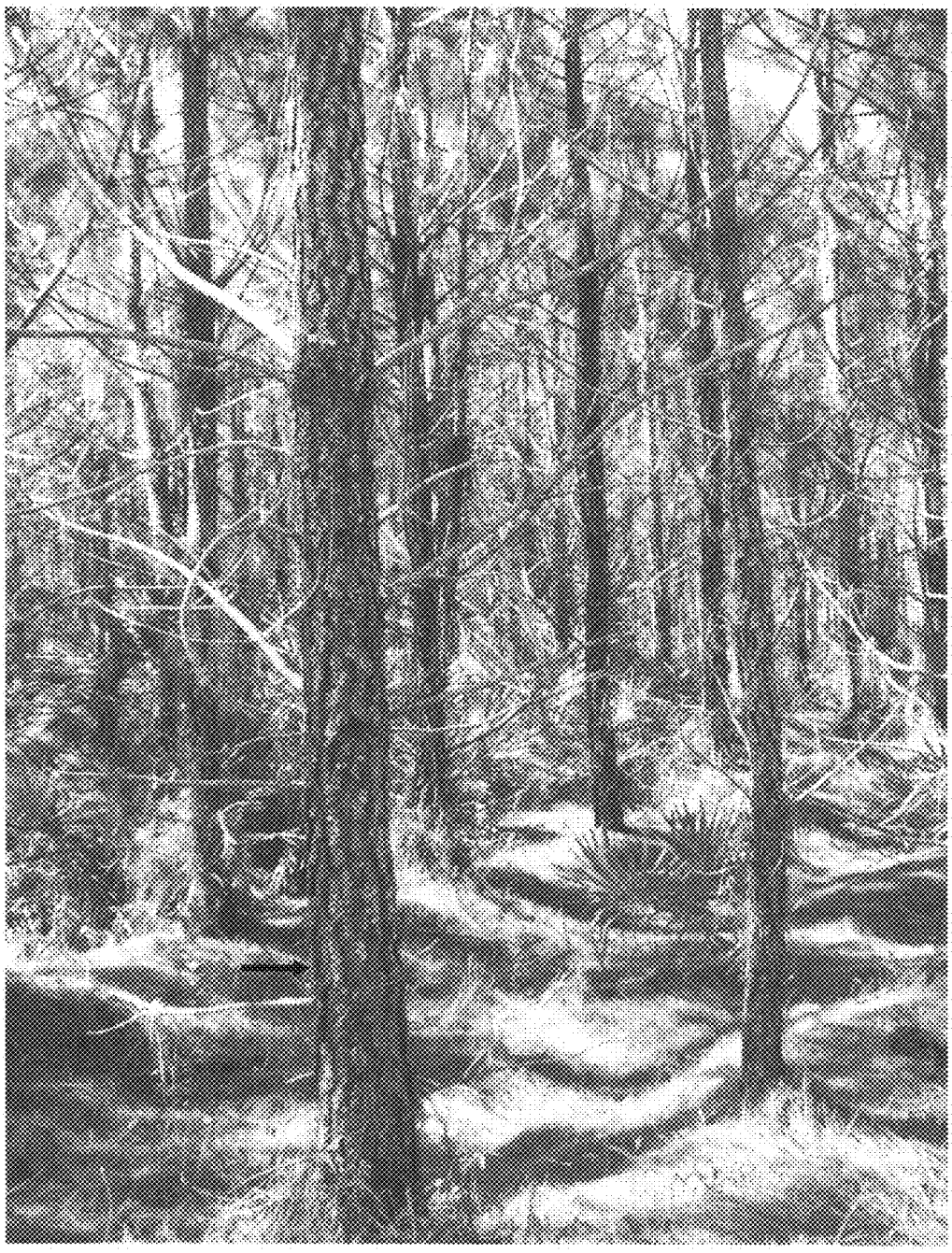
FIG. 2 is a photograph showing 'CF PS1-3352' ramet # 1 planted in Nassau, Fla. The picture was taken after seven field growing seasons. The picture shows superiority of growth and stem straightness.

The botanical details of this new and distinct variety of slash pine tree follow. All color descriptions are made in reference to The Royal Horticultural Society (R.H.S.) Colour Chart (2005).

Parentage:

*Female parent.*—(Unknown) first generation selection made in Taylor County, Fla.

*Male parent.*—(Unknown) first generation selection made in Wayne County, Ga.

Compared to unimproved slash pine trees, 'CF PS1-3352' is characterized by high growth rate, good resistance to fusiform rust (caused by *Cronartium quercuum* (Berk.) Miyabe ex Shirai f. sp. *fusiforme* (Cumm.) Burds. et Snow), good resistance to pitch canker (caused by *Fusarium circinatum* Nirenburg et O'Donnell), excellent stem straightness, medium crown width, long stem internodes, flat to medium branch angle and medium branch diameter.

Average height: 20 ft after 5 field growing seasons
Maximum height: 23 ft after 5 field growing seasons
Average trunk diameter at breast height (4.5 feet above the soil level): 4.1 inches after 5 field growing seasons
Maximum trunk diameter at breast height (4.5 feet above the soil level): 4.8 inches after 5 field growing seasons
Percent stem fusiform rust infection at age 5: 0
Percent branch fusiform rust infection at age 5: 0
Percent branch and stem fusiform rust infection at age 5: 0
Percent dead ramets due to fusiform rust infection at age 5: 0
Percent stem fusiform rust infection in the USDA Resistance Screening Center (Asheville, N.C.) tests after artificial inoculation with rust spores: 15% (compared to 81% infection in unimproved seedlings)
Propagation: Propagated by somatic embryogenesis
Seeds: None produced at age seven years of age, plants are not yet mature. Expected seed production by 12-15 years of age.
Use: High yield industrial plantations
Average branches per whorl: 4.25
Foliage color: Dark green 137A
Branch bark color: Grey N200C / white N155B
Trunk bark color: Grey N200C / grey N155B
Buds color: Yellow brown 167B
Tree shape: Concial with irregular to compact crown
Length of needle: 199.84 mm
Length of sheath: 10.93 mm
Needle thickness: 0.45 mm
Needle diameter: 1.1 mm
Branch diameter: 19.96 mm
Branch angle: 32.17 degrees
Branch angle: 5.01 feet
Branch texture: Rough Descriptions are mean values from five trees measured at age 9.5 years. Branch data is the mean of branches from the whorl immediately above and below a point 8 feet from the base of each tree. Trees were located in Nassau County, Fla. and measurements were recorded on Oct. 31, 2010.

Although the new variety of slash pine tree possesses the detailed characteristics noted above as a result of the growing conditions prevailing in the test locations, it is to be understood that the variations of the usual magnitude and characteristics incident to changes in growing conditions, irrigation, fertilization, pruning, pest control, climatic variations and the like are to be expected. An example of 'CF PS1-3352' can be found at Nassau year 2001 line trial, Nassau county, Fla.

COMPARISON WITH PARENTS BY MICROSATELLITE ANALYSIS

Microsatellite markers were used to generate a unique DNA fingerprint for the variety. Young foliage samples from 5 ramets of PS1-3352 variety and from the parental trees used to make the PS1 cross were collected for DNA fingerprinting. The DNA extraction protocol of Doyle and Doyle (1987) was used after slight modifications. DNA fingerprinting of parents and the PS1-3352 variety was conducted using a set of six microsatellite markers (Echt et al., 2006; Echt et al., 2008). Table 1 shows the sequences and conditions for each primer.

TABLE 1

ID's, sequences and conditions of SSR primers used in slash pine PS1-3352 variety. Ta = primer annealing temperature.

| Primer full ID | UniSTS # | GenBank accession | SEQUENCE (5'-3') | LABEL TAIL (F/R) | MgCl2 (mM) | Ta (° C.) |
|---|---|---|---|---|---|---|
| PtRIP_0619 | 513511 | BV683091 | F:CACGACGTTGTAAAACGAC CAGCTCTCTTAATAGCCTCGG (SEQ ID NO: 1) R:GTTTCTTGCACATAGCAACGCTGAAGA (SEQ ID NO: 2) | F | 2.5 | 65 → 55 |
| PtRIP_1040 | 513556 | BV683133 | F:CACGACGTTGTAAAACGAC TCAAGGAATTCATTGGAGCC (SEQ ID NO: 3) R:GTTTCTTTTTGGCCATATCAAACCCAT (SEQ ID NO: 4) | F | 2.5 | 65 → 55 |
| PtSIFG_0193 | 516249 | BV728742 | F:CACGACGTTGTAAAACGAC CCCATGCATCAATTCAAGTT (SEQ ID NO: 5) R:GTTTCTTTGTGCGTGGATATGGAAAAA (SEQ ID NO: 6) | F | 2.5 | 65 → 55 |
| PtSIFG_0737 | 516298 | BV728669 | F:CACGACGTTGTAAAACGAC GCAAGGGGAATTGCTTATGA (SEQ ID NO: 7) R:GTTTCTTGGGATCGCATCAGCTGTAAT (SEQ ID NO: 8) | F | 2.5 | 65 → 55 |
| PtSIFG_1190 | 516327 | BV728679 | F:CACGACGTTGTAAAACGAC CAGGTGGCTTGGATTTCATT (SEQ ID NO: 9) R:GTTTCTTTCATTCAAGCGTCCTGCTTA (SEQ ID NO: 10) | F | 2.5 | 65 → 55 |

TABLE 1-continued

ID's, sequences and conditions of SSR primers used in slash pine PS1-3352 variety. Ta = primer annealing temperature.

| Primer full ID | UniSTS # | GenBank accession | SEQUENCE (5'-3') | LABEL TAIL (F/R) | MgCl2 (mM) | Ta (° C.) |
|---|---|---|---|---|---|---|
| PtSIFG_4233 | 516353 | BV728685 | F:CACGACGTTGTAAAACGAC AGGGAAACCGCGGATTATAG (SEQ ID NO: 11) R:GTTTCTTCCGGAATGAAGATTGCAGTT (SEQ ID NO: 12) | F | 2.5 | 65 → 55 |

Microsatellite products were detected by M13 tailed primer (Oettling et al., 1995). The amplification products were electrophoresed on 5.5% Long Ranger polyacrylamide gels using a LiCor 4200 automated sequencer (LiCor Inc., Lincoln, Nebr.).

The observed parental genotypes and their expected offspring's genotypes at six studied SSR loci of each family are presented in Table 2. PS1-3352 fingerprint based on 6 loci is presented in Table 3.

TABLE 2

Parental genotypes and their expected offspring's genotypes at six different SSR loci.

| Primer | Genotype Female | Genotype Male | Expected offspring genotypes | | | |
|---|---|---|---|---|---|---|
| PtRIP_0619 | 221/227 | 223/225 | 221/223 | 221/225 | 227/223 | 227/225 |
| PtRIP_1040 | 233/237 | 217/235 | 233/217 | 233/235 | 237/217 | 237/235 |
| PtSIFG_0193 | 256/256 | 256/256 | 256/256 | | | |
| PtSIFG_0737 | 448/460 | 442/448 | 448/442 | 448/448 | 460/442 | 460/448 |
| PtSIFG_1190 | 312/314 | 312/312 | 312/312 | 314/312 | | |
| PtSIFG_4233 | 130/136 | 130/136 | 130/130 | 130/136 | 136/136 | |

TABLE 3

PS1-3352 genotypes at 6 SSR loci. Allelic sizes have LiCor primer tails.

| | PtRIP_0619 | | PtRIP_1040 | | PtSIFG_0193 | |
|---|---|---|---|---|---|---|
| Sample ID | Allele1 | Allele2 | Allele1 | Allele2 | Allele1 | Allele2 |
| PS1-3352 | 221 | 223 | 217 | 237 | 256 | 256 |

TABLE 3-continued

| | PtSIFG_0737 | | PtSIFG_1190 | | PtSIFG_4233 | |
|---|---|---|---|---|---|---|
| Sample ID | Allele1 | Allele2 | Allele1 | Allele2 | Allele1 | Allele2 |
| PS1-3352 | 442 | 448 | 312 | 312 | 130 | 130 |

REFERENCES

Auckland, L., T. Bui, Y. Zhou, M. Shepherd and C. Williams. 2002. Conifer Microsatellite Handbook Corporate Press, Raleigh, N.C., USA.

Doyle, J. J. and J. L. Doyle. 1987. A rapid DNA isolation procedure for small quantities of fresh tissue. Phytochemical bulletin 19:11-15.

Echt, C. S., Nelson, C. D., Erpelding, J. E. and Burns, R. 2006. Southern Institute of Forest Genetics, USDA Forest Service Southern Research Station, 23332 Mississippi 67, Saucier, Miss. 39574, USA. On-line genetic database: http://www.ncbi.nlm.nih.gov/unists Echt, C. S., Saha, S. and Nelson, C. D. 2008. Southern Institute of Forest Genetics, USDA Forest Service Southern Research Station, 23332 Mississippi 67, Saucier, Miss. 39574, USA. On-line genetic database: http://www.ncbi.nlm.nih.gov/unists Oetting, W. S., H. K. Lee, D. J. Flanders, G. L. Wiesner, T. A. Sellers and R. A. King. 1995. Linkage analysis with multiplexed short tandem repeat polymorphisms using infrared florescence and M13 tailed primers. Genomics 30:450-458.

SEQUENCE LISTING

```
<160> NUMBER OF SEQ ID NOS: 12

<210> SEQ ID NO 1
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 1

cacgacgttg taaaacgacc agctctctta atagcctcgg                          40


<210> SEQ ID NO 2
<211> LENGTH: 27
<212> TYPE: DNA
```

-continued

<213> ORGANISM: Artificial Sequence
<220> FEATURE:
<223> OTHER INFORMATION: Synthetic Oligonucleotide

<400> SEQUENCE: 2 gtttcttgca catagcaacg ctgaaga 27

<210> SEQ ID NO 3
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 3 cacgacgttg taaaacgact caaggaattc attggagcc 39

<210> SEQ ID NO 4
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 4 gtttcttttt ggccatatca aacccat 27

<210> SEQ ID NO 5
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 5 cacgacgttg taaaacgacc ccatgcatca attcaagtt 39

<210> SEQ ID NO 6
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 6 gtttctttgt gcgtggatat ggaaaaa 27

<210> SEQ ID NO 7
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 7 cacgacgttg taaaacgacg caaggggaat tgcttatga 39

<210> SEQ ID NO 8
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 8

-continued

```
gtttcttggg atcgcatcag ctgtaat                                        27


<210> SEQ ID NO 9
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 9

cacgacgttg taaaacgacc aggtggcttg gatttcatt                           39


<210> SEQ ID NO 10
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 10

gtttctttca ttcaagcgtc ctgctta                                        27


<210> SEQ ID NO 11
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 11

cacgacgttg taaaacgaca gggaaaccgc ggattatag                           39


<210> SEQ ID NO 12
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 12

gtttcttccg gaatgaagat tgcagtt                                        27
```

We claim:

1. A new and distinct variety of slash pine tree named ‘CF PS1-3352’ substantially as described and illustrated.

* * * * *